United States Patent [19]

Martin

[11] Patent Number: 4,684,346
[45] Date of Patent: Aug. 4, 1987

[54] ENDODONTIC ACCESS BUR WITH EXTENDED DIAMOND COAT AND METHOD FOR USING

[76] Inventor: Howard Martin, 909 Pershing Dr., Silver Spring, Md. 20910

[21] Appl. No.: 757,434

[22] Filed: Jul. 22, 1985

[51] Int. Cl.$^4$ ............................ A61C 3/06; A61C 5/02
[52] U.S. Cl. .................... 433/166; 433/102; 433/224
[58] Field of Search ............... 433/166, 165, 224, 102

[56] References Cited

U.S. PATENT DOCUMENTS

| 477,225 | 6/1892 | Rauhe | 433/165 |
| 2,453,696 | 11/1948 | Brooks | 433/165 |
| 3,534,476 | 10/1970 | Winters | 433/165 |
| 4,190,958 | 3/1980 | Martin et al. | 433/102 |

FOREIGN PATENT DOCUMENTS

| 1294592 | 5/1969 | Fed. Rep. of Germany | 433/166 |
| 392773 | 10/1965 | Switzerland | 433/166 |

OTHER PUBLICATIONS

"ORMCO", Diamond Instruments brochure, 1976, see 'ROUNDS'.

Primary Examiner—John J. Wilson
Attorney, Agent, or Firm—Walter G. Finch

[57] ABSTRACT

The invention concerns a diamond-coated endodontic access bur which is coated at least 10 mm along the shaft. This significant amount of diamond coating along the shaft permits the bur to be used both for dentin removal and finishing the slope and sidewalls of the tooth's pulp chamber. The bur sphere, also diamond coated, has a diameter of 0.5 to 1.0 mm, approximately.

1 Claim, 3 Drawing Figures

ENDODONTIC ACCESS BUR WITH EXTENDED DIAMOND COAT AND METHOD FOR USING

BACKGROUND OF THE INVENTION

The endodontic access cavity is the cavity prepared in the crown of the tooth through which root canal therapy is performed. The establishment of access is the first step in the mechanical phase of endodontics. Also, it is the procedure upon which the rest of endodontic therapy rests. No step of the therapy can be omitted without affecting the entire treatment. Penetration into the pulp chamber is the first step, followed by funneling of the preparation so that the access cavity is smallest at the orifice of the canal and largest at the occlusal opening. The penetration is usually accomplished at the occlusal opening, accomplished with a round carbide bur. The funneling step is done after the roof of the penetrated pulp chamber is peeled back and up, by a withdrawal stroke of the round bur. The round bur or a tapered carbide or diamond is then used to flare or funnel the preparation providing straight access and a positive seat for a filling. Such a straight line access is important for adequate canal penetration without obstructions, which also eliminates overhangs. A great many root canal cases fail because the dentist does not obtain adequate access to the canal. Inadequate access makes proper instrumentation and filling of the canal very difficult. A set of general rules for making occlusal openings for endodontic work can be stated. (1) The opening must extend to the full periphery of the pulp chamber including the pulp horns; (2) direct access to the canal must be obtainable; (3) no overhanging portions of the roof of the pulp chamber should remain which may trap pulp debris and blood; (4) destruction of tooth structure should be avoided. The first requirement is important because a frequent cause of discoloration of pulpless teeth is the trapping of blood and organic debris in the pulp horns. Without adequate access, no canal can be properly filed and filled. Failure to remove all the overhanging denting above the pulp chamber may result in retention of large amounts of blood and organic debris in posterior teeth and lead to residual infection. Excessive destruction of tooth structure may result in fracture of the tooth.

Previously, the dentist used a round bur to form an access and might have tried to use this same bur to funnel the canal. However, this causes grooving of the walls of the pulp chamber and yields incomplete debris removal, which results in a rough inner surface that easily harbors debris and tissue. The dentist also made his penetration with a fissure type bur that funnels and smooths the chamber wall, but tends to cut the floor of the pulp chamber, making it difficult to find the canal openings. A more recent technique involves making an access with a round bur along the floor of the chamber, then, using this bur, strip away the roof. A tapered fissure bur is then used to smooth and funnel the circumferential walls. Thus, the recent technique is a two instrument two step procedure. It is apparent that this technique is more time consuming and more costly than a technique using one instrument for both steps. A diamond carbide combination bur has been developed, but the tip, carbide, wore at a different rate than the diamond and it is not properly sized for root canal work.

All presently available diamond burs differ from the present invention. None has a sufficiently rounded end, nor has an adequate amount of diamond coating up the instrument shaft to allow a dentist to fully prepare the access. Prior art burs are diamond coated approximately 6 mm along the shaft. The present invention concerns a diamond coating of at least 10 mm up the shaft. The round end is the usual equivalent of a #2, #4 and #6 round bur, approximately ½–1 mm in diameter.

SUMMARY OF THE INVENTION

The purpose of the invention, an endodontic access bur having an extended diamond coating, is to combine in one instrument the functions of several that have been previously used for this purpose.

The endodontic access bur in accordance with the invention leads to a smoother penetration of the occlusal surface with less vibration than does the tungsten or carbide burs. The round part of the bur is used to drill through the dentin into the pulp chamber. The bur is then run or brushed across the floor of the pulp chamber without gouging the pulpal floor. Once accomplished the bur is then leaned against the walls of the pulp chamber in a circumferential motion which removes the roof and simultaneously smooths and funnels the lateral walls of the pulp chamber and creates a smooth, accessible and visible access cavity. These steps are accomplished while working from the inside-out, which is considerably easier for the operator while cutting away all the overhanging dentin and smoothing the lateral walls at the same time. This allows easy and proper extension of the internal cavity walls as they relate to the root canal openings. An external projection of the internal anatomy is realized, reducing the propensity to overcut and to remove too much structure from the tooth, thereby weakening it

DETAILED DESCRIPTION OF THE INVENTION

Figure 1:
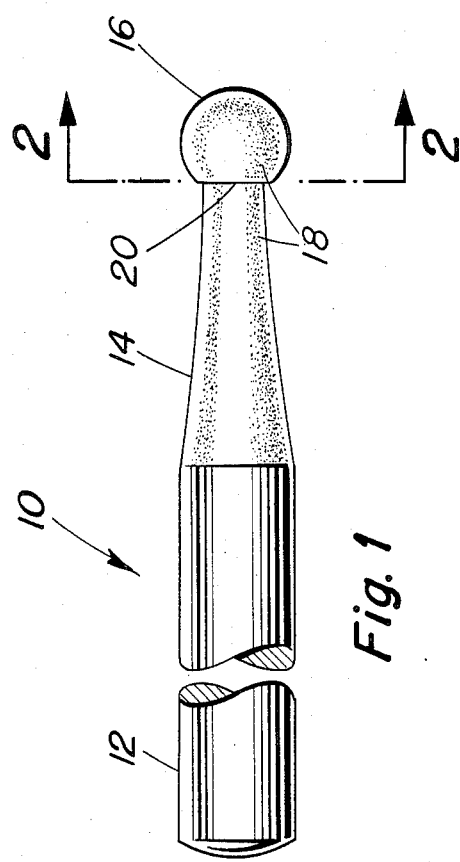
FIG. 1 shows a dental instrument in accordance with the present invention.

FIG. 1 shows the endodontic dental bur, generally at 10. As is typical, the bur 10 includes a cylindrical shank portion 12. Integrally connected to the shank portion 12 is a tapered portion 14, the curved shape of which allows free movement of the instrument in creating an access. It is apparent that the tapered portion 14 curves inward from the shank portion 12 to a sphere 16, the diameter of the tapered portion 14 decreasing non-linearly between these points. The sphere 16, having a diameter of 0.5 to 1.0 mm, approximately, is provided for drilling through dentin into the pulp chamber and is integrally connected to the tapered portion 14. In accordance with the present invention the sphere 16 and tapered shank 14 are coated with diamond. The diamond coating 18 engulfs the sphere 16 and is provided at least 10 mm along the tapered portion 14 from the sphere 16. The provision of at least 10 mm of diamond along the tapered portion 14 is provided to fully prepare the access, as discussed below.

Figure 2:
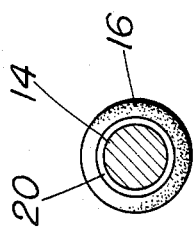
FIG. 2 is a cross-sectional view of the dental instrument of FIG. 1, taken at line 2—2.

FIG. 2 reveals the sphere 16 has a flattened portion 20 (forming a circular plane), where the tapered portion 14 integrally connects to the sphere 16, insuring a solid joint.

Figure 3:
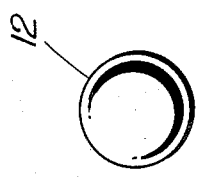
FIG. 3 shows an end view of the instrument of FIG. 1.

FIG. 3 shows an end view of the instrument 10 in a manner which reveals the cylindrical shape of the shank portion 12.

METHOD OF USE

The diamond coated endodontic access bur 10 provides a smoother penetration of the occlusal surface, with less vibration than prior art tungsten or carbide burs. The sphere 16 of the bur is used to drill through the dentin and drop into the pulp chamber. The bur is then run or brushed across the floor of the pulp chamber without gouging the pulpal floor. Once accomplished the bur is then leaned against the walls of the pulp chamber, the tapered portion 14 contacting the walls as necessary, in a circumferential motion to remove the roof and simultaneously smooth and funnel the lateral walls of the pulp chamber. Thus, a smooth, accessible and visible access cavity is created. These steps are accomplished from the inside out, which is considerably easier for the operator while cutting away all the overhanging dentin and smoothing the lateral walls at the same time. This allows easy and proper extension of the internal cavity walls as they relate to the root canal openings. An external projection of the internal anatomy is realized, reducing the propensity to overcut and remove to much structure from the tooth, thereby weakening it.

Other modifications are apparent to those skilled in the art which are in keeping with the spirit of the present invention, the scope of which being defined by the appended claims.

What is claimed is:

1. A dental instrument, comprising, a shank portion;

a tapered portion integrally connected to said shank portion, a sphere integrally connected to said tapered portion opposite said shank portion; with said sphere being approximately 0.5 to 1.00 mm in diameter, said tapered portion being a curved surface curving inwardly from said shank portion toward said sphere; a diamond coating positioned over said sphere and along said tapered portion approximately the length of said tapered portion from said sphere, said diamond coating being at least 10 mm along said tapered portion.

* * * * *